US008871194B2

(12) United States Patent
Hachiya et al.

(10) Patent No.: US 8,871,194 B2
(45) Date of Patent: Oct. 28, 2014

(54) METHOD FOR TRANSFORMING A HAIR FOLLICLE

(75) Inventors: Akira Hachiya, Cincinnati, OH (US); Penkanok Sriwiriyanont, Cincinnati, OH (US)

(73) Assignee: Kao Corporation, Tokyo (JO)

( * ) Notice: Subject to any disclaimer, the term of this patent is extended or adjusted under 35 U.S.C. 154(b) by 0 days.

(21) Appl. No.: 12/010,426

(22) Filed: Jan. 24, 2008

(65) Prior Publication Data

US 2009/0191169 A1    Jul. 30, 2009

(51) Int. Cl.
  *A61K 48/00*    (2006.01)
(52) U.S. Cl.
  USPC ..................................... 424/93.21
(58) Field of Classification Search
  USPC ......... 424/93.21, 93.2; 514/44; 800/8, 18, 21, 800/3, 14, 19
  See application file for complete search history.

(56) References Cited

U.S. PATENT DOCUMENTS

| 6,790,657 B1 * | 9/2004 | Arya .......................... 435/320.1 |
| 6,852,510 B2 * | 2/2005 | Bremel et al. ............... 435/69.1 |
| 7,067,496 B2 | 6/2006 | Saito et al. |

FOREIGN PATENT DOCUMENTS

| EP | 1 306 426 A1 | 5/2003 |
| JP | 2004-500809 A | 1/2004 |
| WO | WO 01/42449 A2 | 6/2001 |

OTHER PUBLICATIONS

Hachiya (Gene Therapy, Feb. 1, 2007, vol. 14, p. 648-656).*
Baek (Human Gene Therapy, 2001, vol. 12, No. 12, p. 1551-1558).*
Setoguchi (J. Investigative Dermatology, 1994, vol. 102, 415-421).*
Cotsarelis, G., "Epithelial Stem Cells: A Folliculocentric View," *J. Invest. Dermatol.* 126:1459-1468, Nature Publishing Group (2006).
Domashenko, A., et al., "Efficient delivery of transgenes to human hair follicle progenitor cells using topical lipoplex," *Nat. Biotech.* 18: 420-423, Nature America Publishing (2000).
Hachiya, A., et al., "Gene Transfer in human skin with different pseudotyped HIV-based vectors," *Gene Ther.* 14:648-656, Nature Publishing Group (Feb. 2007).
Ito, M., et al., "Stem cells in the hair follicle bulge contribute to wound repair but not to homeostasis of the epidermis," *Nat. Med.* 11:1351-1354, Nature Publishing Group (2005).
Kobinger, G.P., et al., "*Filovirus*-pseudotyped lentiviral vector can efficiently and stably transduce airway epithelia in vivo," *Nat. Biotech.* 19:225-230, Nature Publishing Group (2001).
Li, L., and Hoffman, R.M., "The feasibility of targeted selective gene therapy of the hair follicle," *Nat. Med.* 1:705-706, Nature Publishing Group (1995).
Roop, D.R., et al., "An activated Harvey *ras* oncogene produces benign tumours on mouse epidermal tissue," *Nature* 323:822-824, Macmillan Journals Ltd. (1986).
Saito, N., et al., "High efficiency genetic modification of hair follicles and growing hair shafts," *Proc. Natl. Acad. Sci. U.S.A.* 99:13120-13124, National Academy of Sciences (2002).
Weinberg, W.C., et al., "A comparison of interfollicular and hair follicle derived cells as targets for the v-$ras^{Ha}$ oncogene in mouse skin carcinogenesis," *Carciogenesis* 12:1119-1124, Oxford University Press (1991).
English language abstract for JP 2004-500809 A, DWPI Accession: 2001-381676/200864, Thompson Innovation (listed as document FP2 accompanying PTO/SB/08A).
Kuhn, U., et al., "In Vivo Assessment of Gene Delivery to Keratinocytes by Lentiviral Vectors," *J. Virology* 76:1496-1504, American Society for Microbiology, Washington, DC (Feb. 2002).
Schlake, T., "FGF signals specifically regulate the structure of hair shaft medulla via IGF-binding protein 5," *Development* 132:2981-2990, The Company of Biologists, Cambridge, England (Jul. 2005).
Sugiyama-Nakagiri, Y., et al., "Hair follicle stem cell-targeted gene transfer and reconstitution system," *Gene Therapy* 13:732-737, Nature Publishing Group (Apr. 2006).
Weger, N., et al., "IGF-I Signaling Controls the Hair Growth Cycle and the Differentiation of Hair Shafts," *J. Investigative Dermatology* 125:873-882, Nature Publishing Group (Nov. 2005)
International Search Report with its Written Opinion, issued on Mar. 19, 2009, for International Application No. PCT/JP2008/073963.
Cotsarelis, G., "Gene expression profiling gets to the root of human hair follicle stem cells," *J. Clin. Invest.* 116:19-22, American Society for Clinical Investigation (Jan. 2006).
Kunicher, N., et al., "Tropism of Lentiviral Vectors in Skin Tissue," *Human Gene Therapy* 19:255-66, Mary Ann Leibert, Inc. (Mar. 2008)
Kunicher, N., et al, "Characterization of factors that determine lentiviral vector tropism in skin tissue using an ex vivo model," *J. Gene Med.* 13:209-220, John Wiley & Sons, Ltd. (Apr. 2011).
Lyle, S., et al., "The C8/144B monoclonal antibody recognizes cytokeratin 15 and defines the location of human hair follicle stem cells," *J. Cell Science* 111:3179-88, The Company of Biologists Limited (1998).
Paus, R., "A neuroendocrinological perspective on human hair follicle pigmentation," *Pigment Cell Melanoma Res.* 24:89-106, John Wiley & Sons A/S (Nov. 2010).
Sriwiriyanont, P., et al., "Lentiviral Vector-Mediated Gene Transfer to Human Hair Follicles," *J. Invest. Dermatology* 129:2296-99, Nature Publishing Group (Feb. 2009).
Sriwiriyanont, P., et al., "Effects of IGF-Binding Protein 5 in Dysregulating the Shape of Human Hair," *J. Invest. Dermatology* 131:320-328, Nature Publishing Group (Oct. 2010).

(Continued)

*Primary Examiner* — Michael C. Wilson
(74) *Attorney, Agent, or Firm* — Sterne, Kessler, Goldstein & Fox, P.L.L.C.

(57) ABSTRACT

To provide a transformed hair follicle and a method for transferring a gene to a mammal by means of the transformed hair follicle.

The invention provides a method for producing a transformed hair follicle including transferring a gene into a hair follicle by use of a virus vector, characterized by including providing a lentivirus pseudo-typed with VSV-G as a virus vector and transfecting a hair follicle with the lentivirus ex vivo.

12 Claims, 9 Drawing Sheets
(8 of 9 Drawing Sheet(s) Filed in Color)

(56) References Cited

OTHER PUBLICATIONS

Tsuboi, R., et al., "Antisense oligonucleotide targeting fibroblast growth factor receptor (FGFR)-1 stimulates cellular activity of hair follicles in an in vitro organ culture system," *Int. J. Dermatol.* 46:259-63, John Wiley & Sons, Inc. (Mar. 2007), abstract only.

Uchugonova, A., et al., "The bulge area is the origin of nestin-expressing pluripoint stem cells of the hair follicle," *J. Cell. Biochem.* 112:2046-50, John Wiley & Sons, Inc. (Aug. 2011), abstract only.

Westgate, G., "Diversity in Human Hair—The Influences of Biologic and Genetic Variation Among Individuals," *Cosmetiscope* 18:1 & 4-9, New York Society of Cosmetic Chemists (Sep. 2012).

Cotsarelis, G., "Hair follicle stem cells: their location and roles," in: Hair and its Disorders, Biology, Pathology and Management, Camacho et al., eds., Martin Dunitz, London, United Kingdom (2000).

Ghazizadeh, S., et al., "Lentivirus-Mediated Gene Transfer to Human Epidermis," *JID Symposium Proceedings* 9(3):269-275, The Society for Investigative Dermatology, Inc. United States (2004).

Hengge, U.R., "Gene therapy progress and prosepcts: the skin—easily accessible, but still far away," *Gene Therapy* 13:1555-63, Macmillan Press Ltd., Hampshire, UK (2006).

MA, D.R., et al., "A review: the location, molecular characterisation and multipotency of hair follicle epidermal stem cells," *Annals Acad. Med.* 33:784-88, Academy of Medicine, Singapore (2004).

Morris, J.J., et al., "Capturing and profiling adult hair follicle stem cells," *Nat. Biotechnology* 22:411-17, Nature Publishing Company, New York, NY (2004).

Porter, R.M., "Mouse models for human hair loss disorders," *J. Anatomy* 202:125-31, London, Cambridge Univ. Press (2003).

Official Communication issued on Dec. 5, 2012 for European Patent Application No. 08871230.2.

* cited by examiner (A)

(B)

(A)

(B)

METHOD FOR TRANSFORMING A HAIR FOLLICLE

FIELD OF THE INVENTION

The present invention relates to a transformed hair follicle and to a method for transferring a gene to a mammal by means of the transformed hair follicle.

BACKGROUND OF THE INVENTION

In recent years, disease-causing genes, regeneration-related genes, and other analogous genes have been identified, and many pathological conditions and regeneration have been elucidated on the basis of molecular-level mechanisms thereof. Under such circumstances, studies are now carried out on transferring an exogenous gene to cells of patients or other subjects for the treatment of diseases and the regeneration of the organs and tissues of the patients or subjects.

Generally speaking, transfer of an exogenous gene into a cell is performed through known techniques such as lipofection (employing liposome) and use of a virus vector; e.g., an adenovirus vector or a retrovirus vector. Among these techniques, those employing virus vectors are widely applied, from the viewpoint of gene transfer efficiency. In addition, recently, for overcoming a drawback of retrovirus vectors that they can be transferred only into mitotic cells, there have also been employed lentivirus vectors which are constructed through deleting or inactivating a highly hazardous specific sequence in an RNA virus belonging to Retroviridae (e.g., HIV-1). Furthermore, also employed is a pseudo-typed lentivirus vector, whose envelope protein involved in binding on cell surfaces has been altered to the envelope glycoprotein from vesicular stomatitis virus (VSV), the Zaire Ebola (EboZ) virus, or a similar protein so as to enhance transfer efficiency to specific cells. Previous studies in fact revealed that use of EboZ glycoprotein as an envelope protein enhances gene transfer efficiency to human respiratory epithelial cells (Kobinger GP. et al., Nat. Biotechnol. 19: 225-230, (2001)) and that use of VSV-G as an envelope protein enhances gene transfer efficiency to human epidermal stem cells (Hachiya A. et al., Gene Ther. 14: 648-56, (2007)).

Meanwhile, cells of skin tissue present in the body surface are often employed as the cells into which an exogenous gene is transferred, in consideration of convenience, facility, etc. in monitoring during or after gene transfer. Since the epidermis and hair follicles are formed of cells in a terminal differentiation stage, stem cells thereof continually produce new cells (Cotsarelis G., J Invest. Dermatol. 126: 1459-1468, (2006)). Therefore, when an exogenous gene is intended to be expressed for a long period of time, the gene must be transferred into the corresponding stem cells. Hitherto, in the epidermis, stem cells are known to be present in the epidermal basal layer, whereas in hair follicles, stem cells are known to be present in the bulge region.

Since studies elucidated that stem cells of hair follicles play an important role in healing epidermal wounds, as contrasted to general epidermal turnover (Ito M. et al., Nat. Med. 11(12): 1351-1354, (2005)), epidermal cells and melanocyte stem cells present in the bulge region of a hair follicle have become of interest, and transferring a gene into stem cells of a hair follicle has become more and more important.

In other words, if an exogenous gene for promoting healing of wounds is transferred into stem cells in the bulge region, during the healing process, a portion of the epidermis is reconstructed from the stem cells having a newly added function. Thus, a technique of transferring a gene to a stem cell in the bulge region realizes more effective regeneration of the epidermis and is conceivably effective means for gene therapies based on expression of a specific gene in the epidermis.

Regarding lipofection, experimental results of transferring a gene to a tissue containing mouse hair follicles employing liposome trap LacZ are reported (Li L. et al., Nat. Med 1: 705-706 (1995)). Another publication describes that a recipient preferred for a liposome composition is a hair follicle in the growth phase and that, through lipofection, a gene can be transiently transferred into about 10% of hair follicles in a human scalp piece transplanted to an immunodeficient mouse (Domashenko, A. et al., Nat. Biotechnol. 18(4): 420-423, (2000)).

However, since genes are temporarily transferred into cells through lipofection, a problem still remains that the technique does not suit for a long-term expression of a gene.

It has also been reported that when mouse hair follicular tissues are treated with collagenase, followed by transferring a gene by use of an adenovirus vector, the tissue is successfully genetically modified ex vivo, and the thus-modified tissue can be successfully transplanted to sound mammal subjects (WO2001/042449; U.S. Pat. No. 7,067,496; JP 2004-500809; and N. Saito S. et al., PNAS 99(20): 13120-13124, (2002)).

However, even when an adenovirus vector is employed, the transgene is present in episomes, and the expression of the gene is attained only transiently, which also remains as a problem.

It has further been reported that when intact hair follicles are isolated from the mouse dermis through the collagenase treatment, followed by transferring an oncogene thereto by use of a Moloney mouse leukemia retrovirus (MoMLV) vector, cancer can be developed in the gene-transferred tissue in nude mice through transplant thereof (Weinberg W. C. et al., Carcinogenesis 12: 1119-1124, (1991); Roop, D. R. Dennis R. R. et al., Nature 323: 822-824, (1986)). Also reported is that when a tyrosinase gene is transferred into packaging cells by use of a mouse leukemia retrovirus (MLV) vector, followed by co-culturing the packaging cells and a mouse skin tissue, presence of melanin is confirmed in the hair matrix and hair shaft of a mouse hair follicle until day 6 (WO2001/042449; U.S. Pat. No. 7,067,496; and JP 2004-500809).

However, since retrovirus vectors encounter difficulty in gene transfer to non-proliferating cells such as neurocytes, the type of gene-transferable cells is disadvantageously limited. It is generally accepted in the art that when a gene is transferred by use of a retrovirus vector, expression of the transgene is difficult to maintain for a long period of time while preventing the transgene from escaping.

SUMMARY OF THE INVENTION

The present invention is directed to the following:
1. A method for producing a transformed hair follicle including transferring a gene into a hair follicle by use of a virus vector, wherein the method contains: providing a lentivirus pseudo-typed with VSV-G as a virus vector and transfecting a hair follicle with the lentivirus ex vivo.
2. A production method as described in 1 above, wherein the hair follicle is of human origin.
3. A transformed hair follicle produced through the production method as recited in 1 or 2 above.
4. A mammal into which the transformed hair follicle as recited in 3 above has been transplanted.
5. A method for transferring a gene into a mammal comprising the following steps (1) to (3):

(1) a step of producing a lentivirus vector which contains a target gene and which has been pseudo-typed with VSV-G;

(2) a step of transfecting a human hair follicle with the lentivirus vector ex vivo, to thereby produce a transformed hair follicle; and (3) a step of transplanting the transformed hair follicle into an animal.

6. A gene transfer method as described in 5 above, wherein the hair follicle is of human origin.

7. A transformed mammal produced by a gene transfer method as recited in 5 or 6 above.

8. A method for evaluating a function of a test gene including the following steps (1) to (4):

(1) a step of transferring a test gene into a lentivirus vector pseudo-typed with VSV-G;

(2) a step of transfecting a hair follicle with the lentivirus vector ex vivo, to thereby produce a transformed hair follicle;

(3) a step of transplanting the transformed hair follicle into a test animal; and (4) a step of determining the shape and properties of hair regenerated from the hair follicle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
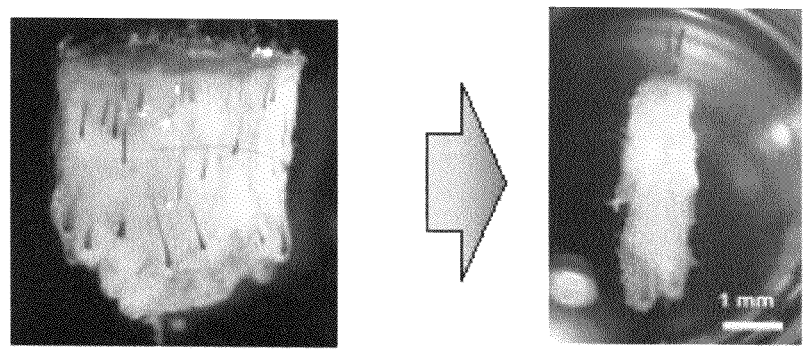
FIG. 1. Hair follicle trimmed to an apple-shape.

The present invention is directed to a transformed hair follicle and to a method for transferring a gene into a mammal by means of the transformed hair follicle.

The present inventors have carried out extensive studies on gene transfer to hair follicles, and have found that through transfecting a tissue containing human hair follicles with a VSV-G pseudo-type virus vector ex vivo, a target gene can be effectively transferred into hair follicles, and that by use of the transformed hair follicles, the target gene can be transferred into a test animal at high probability, whereby the transgene can be effectively expressed, and high expression level can be maintained for a long period of time while preventing the transgene from escaping.

According to the present invention, a gene can be transferred into human hair follicles in a simple manner, to thereby produce transformed hair follicles. By use of the transformed hair follicles, a target gene can be effectively transferred into animals, whereby various pathological conditions can be ameliorated, and various diseases can be prevented or treated, over a long period of time. Through employment of the gene transfer method of the present invention, for example, functions of a human gene which has been transferred into a test animal can be evaluated over a long period of time.

The transformed hair follicle of the present invention is produced by providing a lentivirus pseudo-typed with VSV-G as a vector and transfecting a tissue containing a hair follicle with the lentivirus vector ex vivo.

The lentivirus vector pseudo-typed with VSV-G is an HIV-based lentivirus vector in which the envelope glycoprotein has been substituted by an envelope glycoprotein originating from vesicular stomatitis virus (VSV).

No particular limitation is imposed on the lentivirus vector, so long as the vector is generally employed in gene transfer and has an envelope protein pseudo-typed with VSV-G but has no productivity for virus particles having replication ability.

No particular limitation is imposed on the method for producing the lentivirus, and any known methods may be employed. The following is an exemplary method.

The lentivirus is produced based on the so-called triple transfection principle. Therefore, three vectors; i.e., pCMVΔR8.2 having an HIV helper function, a pHxLacZWP transfer vector encoding β-galactosidase, and a vector expressing VSV-G, must be provided. These vectors to be employed may be available from Public Health Agency of Canada (Dr. Kobinger) or University of Pennsylvania Health System (Dr. Wilson).

No particular limitation is imposed on the animal cells for use in the production of the virus, and any animal cells may be used, so long as the animal cells are generally employed in the production of Lentivirus. However, among them, 293T cell is preferred, from the viewpoints of cell culture, nucleic acid transfer facility, virus particle productivity, etc.

When a lentivirus is produced by use of 293T cells, the calcium phosphate precipitation method (provided by Clontech) or an Effectene reagent (provided by Qiagen (Valencia, Calif.)) is employed. In either case, the proportions of VSV-G-expressing vector, pCMVΔR8.2, and pHxLacZWP transfer vector are adjusted to 3:1:2. When the calcium phosphate precipitation method is employed, the endotoxin-free vector mixture (10 μg or 180 μg) is added to 293T cells which have been seeded onto a plate (60 mm or 150 mm). When an Effectene reagent is added to a 10-μg vector mixture, lipid (40 μL), a buffer for concentrating the vectors (800 μL), and an enhancer (55 μL) must be added together. When an Effectene reagent is added to a 180-μg vector mixture, lipid (2.9 mL), a buffer for concentrating the vectors (58 mL), and an enhancer (4 mL) are must be added together. Forty-four Hours after addition, a medium is added to each plate, followed by culturing for 16 hours. The culture containing virus-like particles is filtered by means of a 0.45-μm filter, and the titer is determined through a conventional method. The cell-free viral supernatant is concentrated through ultracentrifugation (4° C., 28,000 rpm) for two hours and re-suspended in DMEM (Dulbecco's modified Eagle's medium (Invitrogen, Calsbard, Calif.)).

The suspension can be stored at −80° C. before use thereof. It is noted that the viral stock suspension thus obtained is to be verified to include no replicable lentivirus by culturing MT4 or 293T cells infected with the virus in the stock suspension for 30 days and detecting the expression of p24 antigen in the culture.

One exemplary method for producing a lentivirus other than the aforementioned method is a method disclosed in JP 2005-533485.

Examples of the target (exogenous) gene to be transferred include a gene encoding a protein controlling hair growth or hair quality (color, straight or curly nature, density, etc.) or a fragment thereof, a gene encoding a hormone- or disease-related protein or a fragment thereof, and a gene relating to promotion of healing wounds or a fragment thereof.

In the case of gene function analysis, no particular limitation is imposed on the gene to be transferred. However, for enhancing a function of a target gene, the target gene is preferably transferred with a promoter sequence. Examples of the promoter sequence include those expressing the gene under all conditions, those histospecifically expressing the gene, and those expressing the gene when induced by a drug. For reducing a function of a target gene, the promoter sequence is preferably transferred with another sequence; for example, a sequence encoding siRNA of the target gene, an anti-sense sequence, or a sequence encoding a dominant negative form of a target gene product.

These fragments refer to nucleotide sequences each containing a region at least expressing a target function.

The hair follicle employed in the present invention may be collected from the skin of human or an animal such as a mouse, a pig, or a monkey and is preferably a hair follicle originating from a mammal, more preferably human.

As used herein, the term "hair follicle" refers in a narrower sense to a scalp part including (from the hair shaft side) medulla, inner root sheath (IRS), outer root sheath (ORS), vitreous membrane, and hair follicle of connective tissue nature. However, unless otherwise specified, the term "hair follicle" refers in a broader sense to a tissue surrounding the entirety of the hair root collected from the skin of human or other animals (hereinafter referred to as "hair follicular organ"); i.e., the entirety of the tissue at least including hair-growth-related organs such as the hair shaft, dermal papilla, hair matrix cells, hair root, etc.

The term "tissue including a hair follicle" refers to the entirety of the tissue including a hair follicle and peripheral skin tissue (the epidermis, dermis, panniculus, etc.).

Use of the hair follicular tissue enhances the success rate of transplant. In a preferred mode, the transplant efficiency can be further enhanced by trimming the tissue so as to assume an apple-shape as shown in FIG. 1. From the viewpoint of enhancing transplant efficiency, adipose tissue is preferably removed to a certain extent, as shown in FIG. 1. When organ culturing is performed, the hair follicular tissue is preferably trimmed as completely as possible, since damage during transplant to a mammal subject does not need to be taken into consideration.

The term "apple-shape" refers to a generally round columnar shape of the hair follicular organ to which a tiny volume of peripheral tissue remains attached. The dimensions of a tissue sample containing a hair follicle may be appropriately adjusted in accordance with the type of the hair follicular tissue employed. In the case of human hair follicular tissue, the sample preferably has a diameter of 3 to 5 mm and a length of 5 to 15 mm.

Regarding hair cycle, the hair follicle may be in anagen phase or in catagen phase. Anagen phase is preferred, since a skin piece collected from a donor can be directly tissue-cultured. Even when the hair follicle is not in anagen phase, induction of anagen phase may also be possible. Specifically, in one possible procedure, hair is removed from the skin through the wax method. After hair growth has been established, a skin piece containing a hair follicle is collected at an appropriate point of time. Generally, when mouse subjects are employed, the timing of collection is day 3 to day 10, preferably day 5 to day 7, more preferably day 6. When other mammal subjects are employed, the timing may be determined in consideration of a period required for the establishment of hair growth.

Examples of the animal into which a collected hair follicle is transplanted include animals such as a monkey, a dog, a cat, a sheep and a horse, and laboratory animals such as a rabbit, a mouse and a rat. Needless to say, a collected hair follicle can be transplanted to human subjects.

The gene transfer into hair follicles according to the present invention employing a virus vector is performed by transfecting a tissue containing a hair follicle with the virus ex vivo. Since the virus vector realizes direct transfection of the hair follicle, the method of the invention is more excellent in operability than a conventional method employing a retrovirus; e.g., a method in which a gene is transferred into packaging cells by use of a retrovisus, and the gene-transferred packaging cells and a piece of mouse skin tissue are co-cultured, to thereby transfer the gene to the mouse tissue (see, for example, U.S. Pat. No. 7,067,496).

The cell present in a hair follicle into which an exogenous gene is transferred is most preferably a stem cell present in the bulge region. A precursor cell originating from the stem cell is also preferred. The stem cell plays a role in feeding cells during a development process and in maintenance of tissue/organs. Therefore, when a gene is transferred into stem cells, the transgene is effectively expressed and maintains high expression level while preventing the transgene from escaping, over a long period of time.

In one specific transfection procedure, a hair follicle or a tissue containing a hair follicle, which has been prepared, is immersed in a lentivirus titer liquid, followed by culturing in a hair follicular organ culture medium, to thereby perform transformation.

Examples of the medium include RPMI 1640 medium, William's E medium, and DMEM/HamF12 (1:1) medium. Agar or gelatin may be appropriately added to the medium. If required, an antibiotic, amino acid, blood serum, a growth factor, a bio-extract, etc. may also be added to the medium.

In one exemplary culturing procedure, the hair follicular organ which has been immersed in a lentivirus titer liquid is cultured in an incubator at 37° C. in a 5%-$CO_2$ atmosphere, using a phenol red-free William's E medium (Sigma, St. Louis, Mo.) to which there have been added 2 mM L-glutamine (Invitrogen), 10 µg/mL insulin (Invitrogen), 10 µg/mL transferrin (Invitrogen), 10 ng/mL sodium selenate (Sigma), 10 ng/mL hydrocortisone (Invitrogen), and antibiotics and antimycotics (Invitrogen).

No particular limitation is imposed on the number of times of transfection. However, the number of times is preferably 2 to 3, more preferably 2, in consideration of the copy number of the target gene and damage of hair follicles caused by transfection.

When transfection is carried out twice, the second transfection is preferably performed after culturing for 15 to 20 hours, which has been performed after the first transfection, in order to prevent fatal damage of hair follicles which would otherwise be caused by the virus vector.

In gene-transfer methods employing an adenovirus vector, treatment of hair follicles with collagenase is known to enhance efficiency of transfer of a target gene (Saito N. et al., PNAS. 99(20): 13120-4, (2002)). However, the collagenase treatment, which may destroy the cultured cells, must be performed carefully. According to the method of the present invention employing a lentivirus vector, transfection can be effectively performed without performing any collagenase treatment.

The thus-produced transformed hair follicle is transplanted to an animal (recipient) of interest. Hair follicles or a tissue containing hair follicles may be transplanted to a recipient through a known method. In one preferred method, a hole is provided through the skin to the fascia of a recipient, a hair follicular organ culture medium is added through the hole, a transformed hair follicle is added, and the added hair follicle is immobilized to the skin by use of an instantaneous adhesive for biological use.

For example, when a transformed hair follicle is transplanted to laboratory mice, a hole (diameter: 1 to 2 mm, depth: 10 to 20 mm) is made through the back skin to the fascia of each mouse such that the hole axis is parallel to the mouse's hair shaft, a hair follicular organ culture medium is added through the hole, a transformed hair follicle is inserted, and the inserted hair follicle is immobilized to the skin by use of an instantaneous adhesive for biological use. Through this procedure, in a few months after transplant, hair can be regenerated, and the regenerated hair maintains the morphological characteristics of the donor hair.

The subject serving as a recipient is selected from the aforementioned mammals and human. In order to prevent rejection of the transplanted tissue, the recipient is preferably the same type as the hair follicle donor animal. In the case of a human subject, a hair follicle collected from the same subject is preferably used. When a hair follicle collected from other subjects is used, transplant may be performed with administration of an immunosuppressant or the like. In the latter case, an immunodeficient animal such as a SCID mouse or a nude mouse may be employed as a recipient.

The gene transfer method of the present invention may also be applied to a method for evaluating a function of a test gene. Specifically, through application, to laboratory animals, of a transformed hair follicle into which a test gene has been transferred through the aforementioned method, the effect of a protein or the like expressed by the transferred test gene can also be evaluated. According to the method of the present invention, a test gene is possibly transferred into stem cells in a hair follicle. Therefore, a function of the test gene can be expressed for a long period of time, and the effect of the function can be evaluated for a long period of time. Needless to say, a transformed laboratory animal can also be obtained.

No particular limitation is imposed on the test gene, and any of the aforementioned genes may be employed. The method of evaluating the function may be performed through a conventionally employed evaluation technique selected in accordance with the type of the transgene. The test gene may be known or unknown. However, a known test gene whose function is unknown or an unknown test gene is preferred. Particularly when a gene relating to hair properties including morphological characteristics is tested, the test gene includes a known gene relating to hair properties including morphological characteristics, a known gene whose function is unknown, and an unknown gene which conceivably relates to hair properties including morphological characteristics. Specific examples of the test gene include a gene controlling hair cycle and a gene controlling hair properties including color and morphological characteristics.

When a function of a gene relating to hair properties including morphological characteristics is evaluated, for example, properties including morphological characteristics of the hair regenerated from the hair follicles are determined. Particularly when the hair follicles have not yet been transplanted to a subject (recipient), the hair follicular organ is analyzed during organ culturing in terms of growth (length) of hair shafts, a change (decrease or increase) in diameter of hair shafts, and bending feature of hair follicles, through graphic analysis, measurement by use of a micrometer under a microscope, counting apoptosis cells in the hair follicular organ, etc. After transplant, hair properties such as length from the regenerated hair root to the tip of the hair shaft, diameter (cross-section) of the hair shaft, hair growth rate, color tone, curling degree, and other properties are evaluated directly or through graphic analysis.

Through the aforementioned analyses, hair growth status (growth rate, thickness, etc.), color, hair properties including morphological characteristics (curly or straight), and other properties can be evaluated.

In addition, the method of the present invention can be applied to the gene therapy of hair-related diseases by effectively and efficiently evaluating an improvement of growth, color and properties of human hair grown after transfer of an exogenous gene through the aforementioned analyses.

The present invention will next be described in more detail by way of examples, which should not be construed as limiting the invention thereto.

EXAMPLES

Example 1

Method for Transferring a Gene into Hair Follicles (1) Preparation of a Skin Tissue Sample Containing Hair Follicles Scalp samples were obtained from a Caucasian subject through punch biopsy. This operation was carried out by Stephens & Associates (S&A) (contract laboratory, Dallas).

Specifically, two scalp tissue pieces were obtained from one subject through punch biopsy (diameter of punch: 4 mm). The tissue pieces were transported while they were immersed in DMEM containing an antibacterial agent at 4° C. As soon as the tissue pieces had arrived, adipose tissue was removed from each tissue piece under a dissecting microscope, and the piece was trimmed as shown in FIG. 1, to thereby prepare a skin tissue sample containing hair follicles and having an apple-shape (dimensions: 3 to 5 mm in diameter and 5 to 15 mm in length).

(2) Production of a Virus Vector

A lentivirus pseudo-typed with VSV-G (an HIV-based lentivirus vector whose envelope protein has been substituted by vesicular stomatitis virus glycoprotein (VSV-G)) was obtained from Public Health Agency of Canada (Dr. Kobinger) and stored at −80° C. until use thereof.

An exemplary method of producing the virus vector will next be described.

A lentivirus vector pseudo-typed with VSV-G was produced by simultaneously transferring three vectors (i.e., pCMVΔR8.2 having an HIV helper function, a pHxLacZWP transfer vector encoding β-galactosidase, and a pMD.G vector for expressing a VSV-G envelope protein) into 293T cells. When a lentivirus is produced by use of 293T cells, the calcium phosphate precipitation method (provided by Clontech) or an Effectene reagent (provided by Qiagen (Valencia, Calif.)) is employed. In either case, the proportions of VSV-G-expressing vector, pCMVΔR8.2, and pHR'LacZ transfer vector are adjusted to 3:1:2. When the calcium phosphate precipitation method is employed, the endotoxin-free vector mixture (10 μg or 180 μg) is added to 293T cells which have been seeded onto a plate (60 mm or 150 mm). When an Effectene reagent is added to a 10-μg vector mixture, lipid (40 μL), a buffer for concentrating the vectors (800 μL), and an enhancer (55 μL) are must be added together. When an Effectene reagent is added to a 180-μg vector mixture, lipid (2.9 mL), a buffer for concentrating the vectors (58 mL), and an enhancer (4 mL) are must be added together. Forty-four hours after addition, a medium is added to each plate, followed by culturing for 16 hours. The culture medium containing virus-like particles is filtered by means of a 0.45-μm filter, and the titer is determined through a conventional method. The cell-free viral supernatant is concentrated through ultracentrifugation (4° C., 28,000 rpm) for two hours and re-suspended in DMEM (Dulbecco's modified Eagle's medium (Invitrogen, Calsbard, Calif.)). The suspension can be stored at −80° C. before use thereof. It is noted that the viral stock suspension thus obtained is to be verified to include no replicable lentivirus by culturing MT4 or 293T cells infected with the virus in the stock suspension for 30 days and detecting the expression of p24 antigen in the culture.

(3) Transformation

A $10^9$-order lentivirus titer liquid was prepared. Each of the above-prepared skin tissue samples containing hair follicles was immersed in the titer liquid for four hours, followed by culturing in a hair follicular organ culture medium at 37° C. under a 5%-$CO_2$ atmosphere.

After culturing for 19 hours, second transfection was carried out through immersing in the same titer liquid. After second transfection, organ culturing was continued in the same medium for 14 to 35 days.

Hair follicular organ culture medium: phenol red-free Williams E medium (Sigma, St. Louis, Mo.) supplemented with 2 mM L-glutamine (Invitrogen, Carlsbad, Calif.), 10-μg/mL insulin (Invitrogen), 10-μg/mL transferrin (Invitrogen), 10-ng/mL sodium selenate (Sigma), 10-ng/mL hydrocortisone (Invitrogen) and antibiotics antimycotics (Invitrogen).

(4) Transplant

After transfection with the lentivirus, a hole (diameter: about 1 mm, depth: about 10 to 20 mm) was made by means of a 18 G syringe (diameter: 1 mm) through the back skin to the fascia of an immunodeficient (severe combined immunodeficient; SCID) mouse such that the hole axis is parallel to the mouse's hair shaft. A hair follicular organ culture medium (about 25 μL) was added through the hole, and a transformed hair follicle was inserted into the hole. The inserted hair follicle was immobilized to the skin by use of an instantaneous adhesive for biological use.

Figure 2:
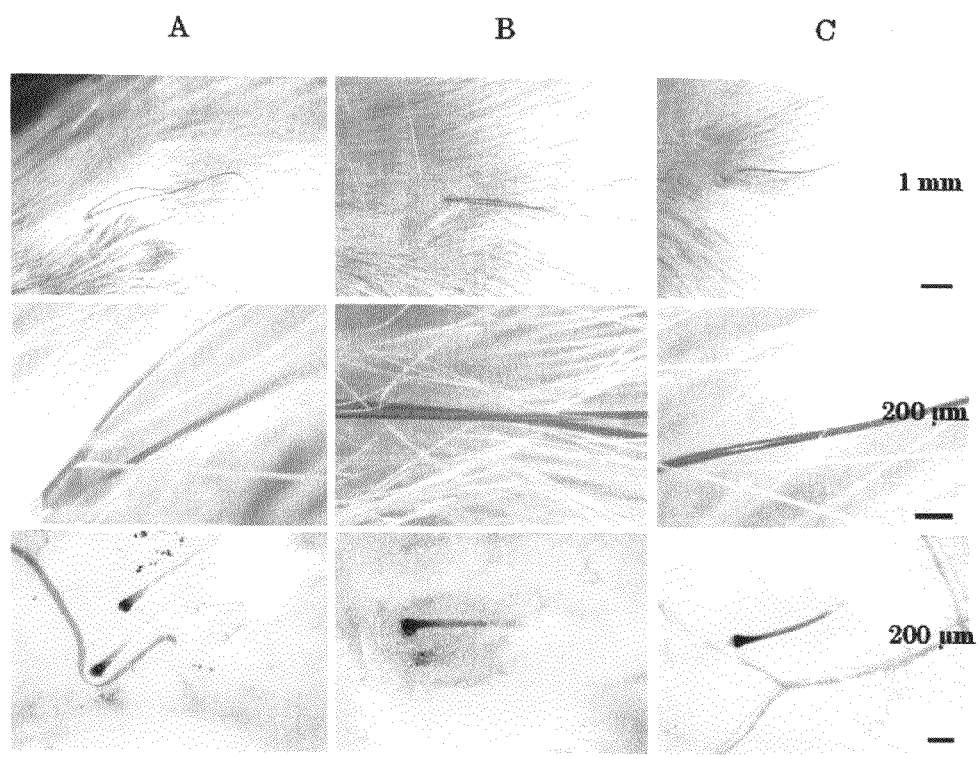
FIG. 2. Hair regenerated about three months after transplant:
  A: a scalp sample containing Caucasian straight hair was divided into four equal parts, and one of the parts was transplanted. After observing regeneration of hair, a lentivirus was intradermally administered at an interval of one week;
  B: Caucasian straight hair follicles were transplanted; and
  C: Caucasian curly hair follicles were transplanted.

Through this procedure, most of the hair follicles were found to regenerate hair about three months after transplant (FIGS. 2B and 2C). The thus-regenerated hair maintained the morphological characteristics of the donor hair.

Referential Example 1

Observation of Tissue Containing Hair Follicles

A hair follicle tissue sample collected through punch biopsy was divided into four equal parts in terms of scalp area (diameter: 2 to 3 mm) (not trimmed to an apple-shape). In a manner similar to that of Example 1, divided parts were transformed, and each transformed tissue sample was transplanted to a mouse.

In Reference Example, the transplanted straight hair was regenerated as curly hair. The hair was curled by tension of the mouse skin (FIG. 2A).

Example 2

Effect of the Number of Transfection Times on Hair Follicles

For evaluating damage of hair follicles caused by transfection with a lentivirus, hair follicle growth rate, amount of conversion of glucose to lactic acid in a hair follicle culture medium, and apoptosis state of a hair follicle were analyzed.

(1) Hair Follicle Growth Rate

The hair follicle growth rate was determined once a week by means of a micrograph and a SPOT software (Diagnostic Instruments, Sterling Heights, Mich.).

Figure 3:
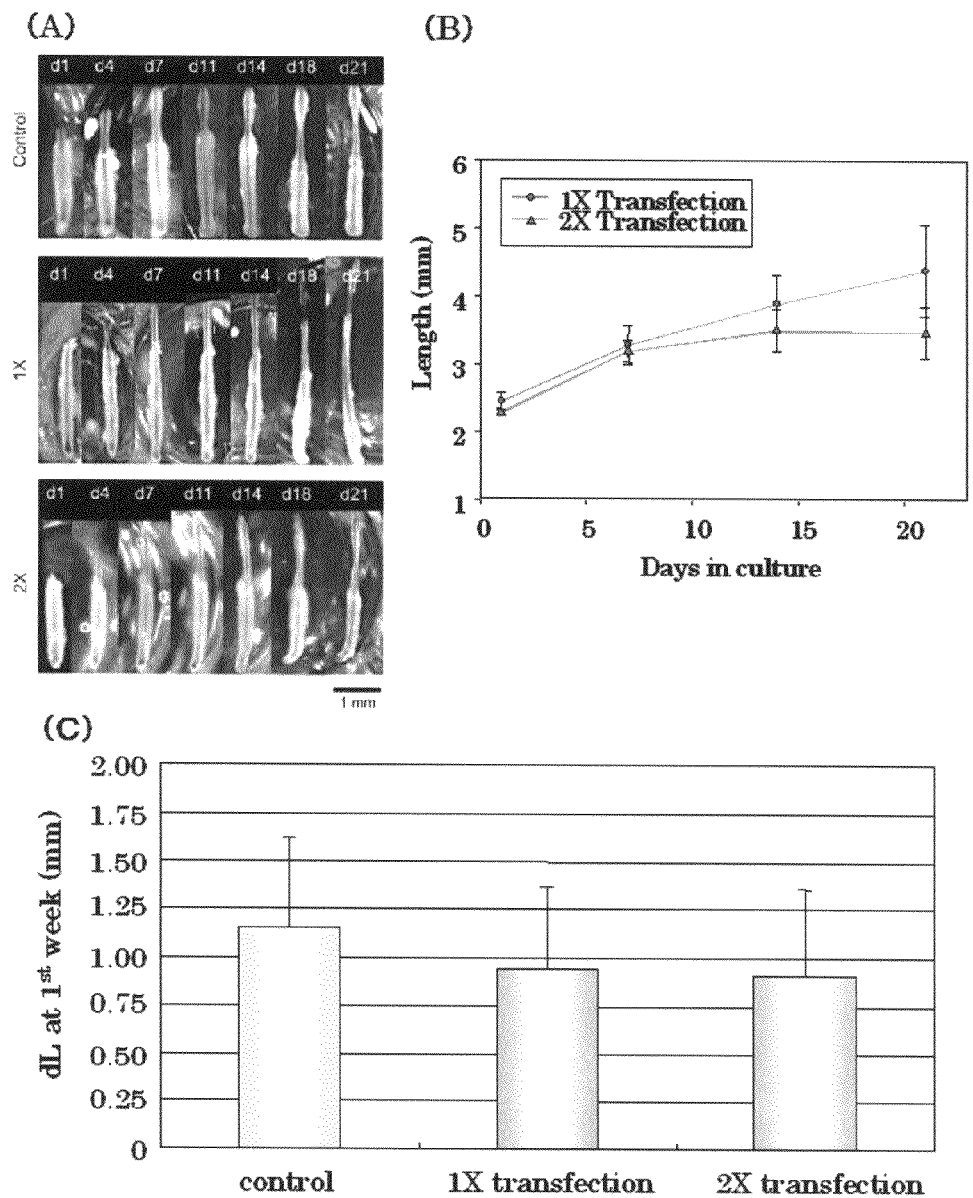
FIG. 3. Organ culturing of an isolated hair follicle after transfection with lentivirus:
  A: appearance to culture day 21;
  B: comparison (on culture day 21) of a hair follicle transfected once and that transfected twice; and
  C: growth rates in culture week 1.

In week 1 from the start of organ culturing, the growth rate was compared among a non-transfected hair follicle (control), a hair follicle transfected once, and a hair follicle transfected twice. Although the difference was not significant, the growth rate was found to be retarded by transfection (FIG. 3). Thereafter, from week 2, the growth rate was compared between the hair follicle transfected once and the hair follicle transfected twice. As a result, the hair follicle transfected twice exhibited reduced growth from day 14 as compared with the hair follicle transfected once, and no growth was observed on day 21.

(2) Amount of Conversion of Glucose to Lactic Acid in a Culture

The amount of glucose consumed and that of lactic acid produced in the culture were determined by means of a 2300 STAT Plus glucose and lactate analyzer (YSI, Inc., Yellow Springs, Ohio).

Figure 4:
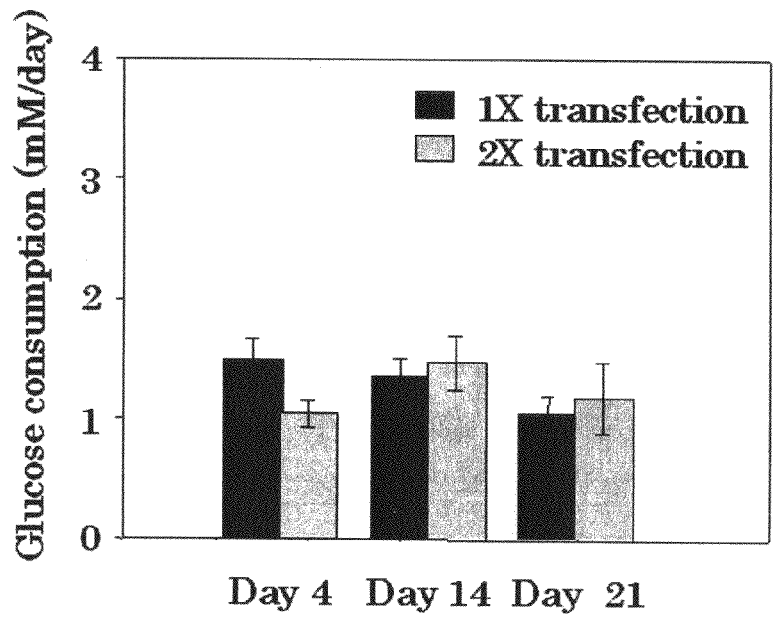
FIG. 4. Amount of glucose consumed and that of lactic acid produced in a hair follicle transfected once and that transfected twice:
  A: Amount of glucose consumption; and
  B: Amount of lactate production.
Figure 4:
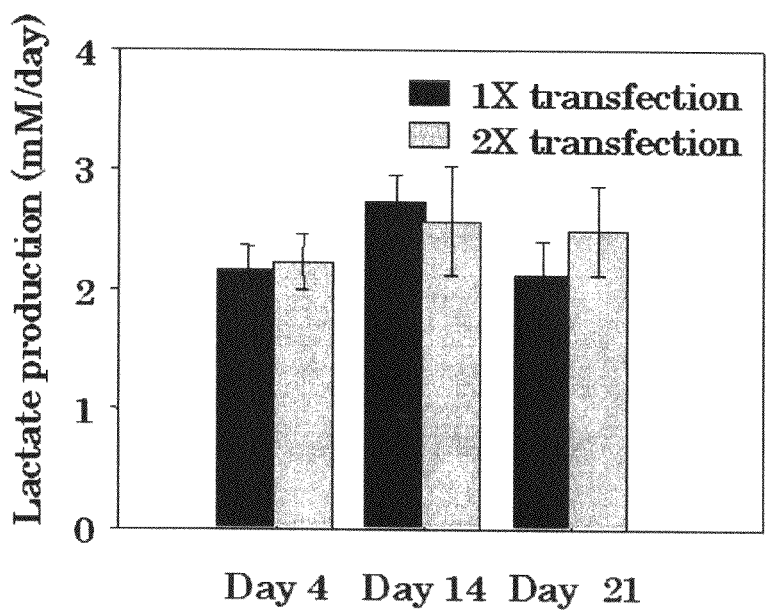

By use of a hair follicle transfected once and a hair follicle transfected twice, the daily amount of conversion of glucose to lactic acid on day 4, day 14, and day 21 were determined. No difference was found in conversion amount between the two groups at any measurement days (FIG. 4).

(3) Apoptosis State of a Hair Follicle

The state of apoptosis of hair follicles was observed by means of an ApopTaq® In Situ apoptosis detection kit (Chemicon, Temecula, Calif.).

Figure 5:
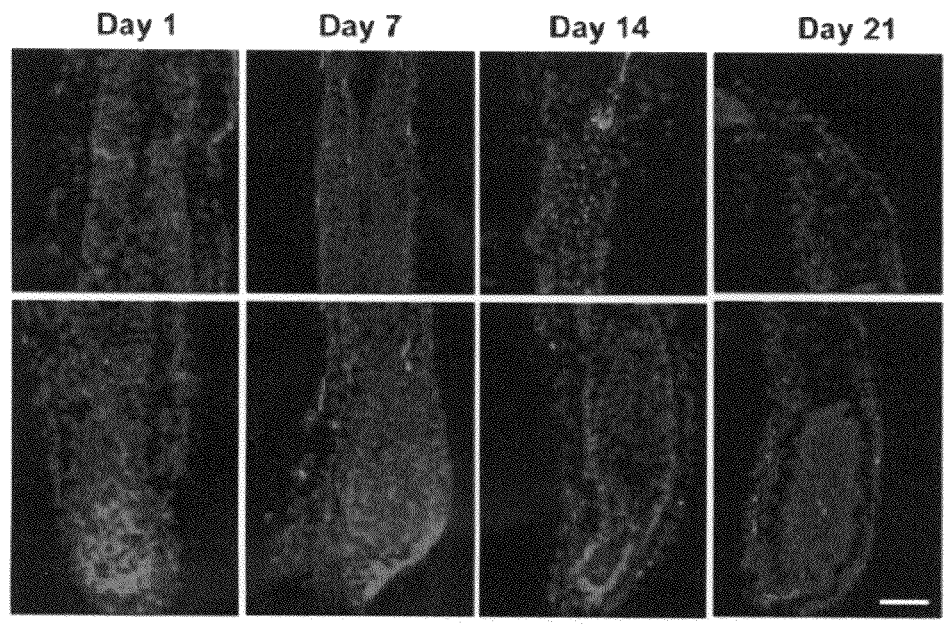
FIG. 5. State of apoptosis in a non-transfected hair follicle, a hair follicle transfected once, and a hair follicle transfected twice:
  A: time-over change in apoptosis status of a non-transfected hair follicle; and
  B: comparison of apoptosis on organ culturing day 14.
Figure 5:
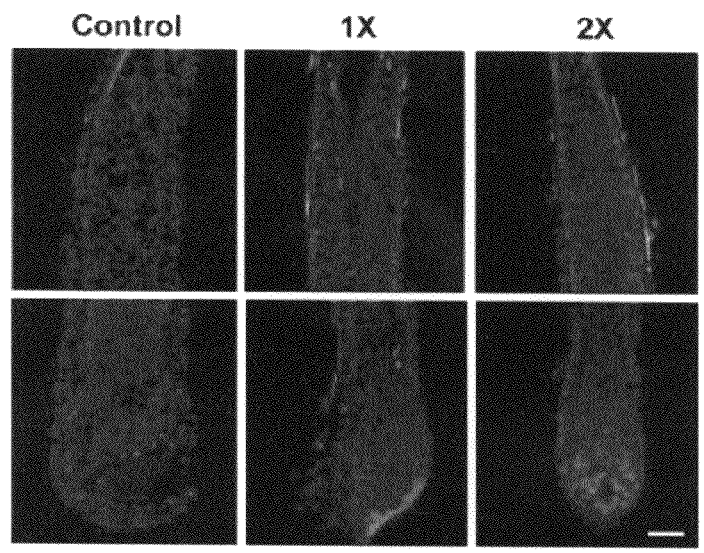

Time-over change in apoptosis status of a non-transfected hair follicle was observed. As shown in FIG. 5A, the red-colored area representing apoptosis increased as time elapsed. Particularly on day 14, the hair bulb was in the regression phase. Based on this observation, the state of apoptosis on day 14 was compared among a non-transfected hair follicle (control), a hair follicle transfected once, and a hair follicle transfected twice. No difference was observed in apoptosis status (FIG. 5B).

As described above, transfection with a lentivirus slightly affects growth of hair follicles, but the retardation was not significant, as compared with the change in hair cycle during organ culturing. Within a period to day 14 (i.e., entrance to the catagen phase), as mentioned hereinbelow, transfection with a lentivirus is considered to be carried out preferably twice.

Example 3

Determination of Gene Transfer Efficiency

After organ culturing for 14 days according to the method described in Example 1 had been completed, gene transfer efficiency of a transformed hair follicle into which a gene (β-galactosidase) had been transferred was determined by use of X-gal, which is a substrate with respect to β-galactosidase.

Specifically, transformed hair follicles were washed thrice with phosphate buffer (PBS) and fixed with 0.1% glutaraldehyde. The fixed product was incubated for 18 hours in a 1 mg/mL X-gal solution diluted with a 0.1M phosphate buffer (pH 7.4) containing 5 mM $K_3Fe(CN)_6$, 5 mM $K_4Fe(CN)_6$, 1 mM $MgCl_2$, 0.02% NP-40, and 0.01% deoxycholate.

Figure 6:
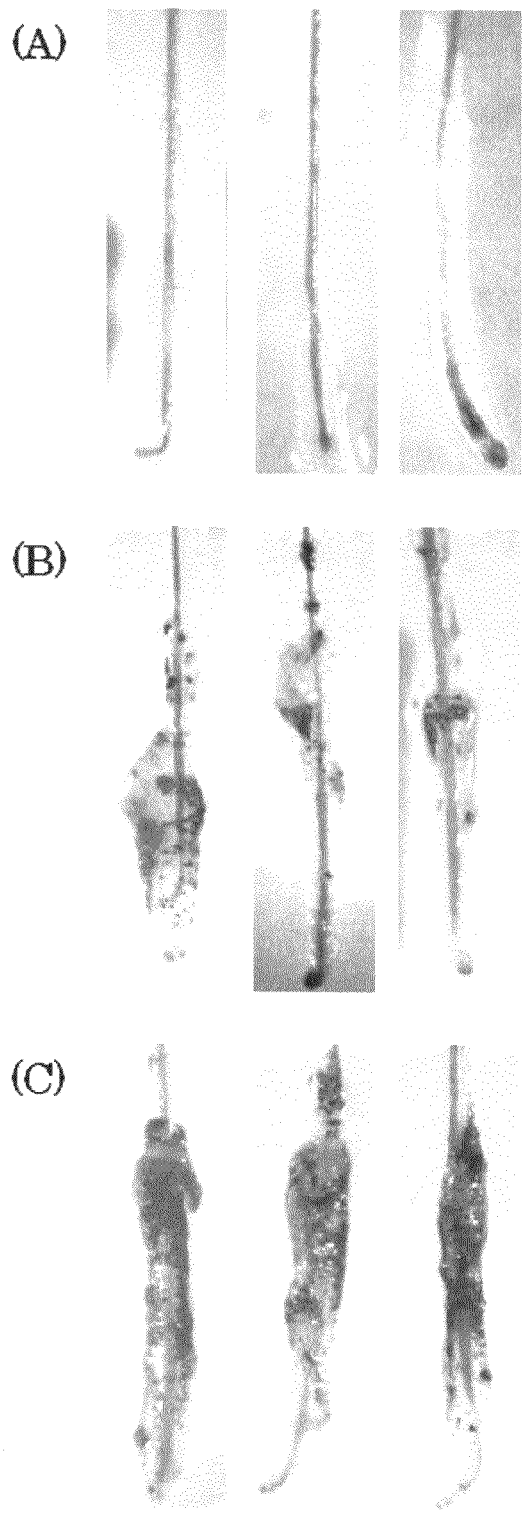
FIG. 6. X-gal staining (on organ culturing day 14) of a non-transfected hair follicle, a hair follicle transfected once, and a hair follicle transfected twice:
  A: non-transfected hair follicles;
  B: hair follicles transfected once; and
  C: hair follicles transfected twice.

The results are shown in FIG. 6. As the blue-colored area increases, gene transfer efficiency increases. A hair follicle which had been transfected twice exhibited color (blue) development in its entirety, indicating that a gene-transfer efficiency in response to the number of times of transfection was observed.

Subsequently, through immunohistological analysis, the site where the exogenous gene is expressed in a hair follicle was investigated.

A transformed hair follicle was cut along a horizontal or perpendicular direction, to thereby prepare slices. Gene expression site was analyzed by use of an antibody to β-galactosidase.

Figure 7:
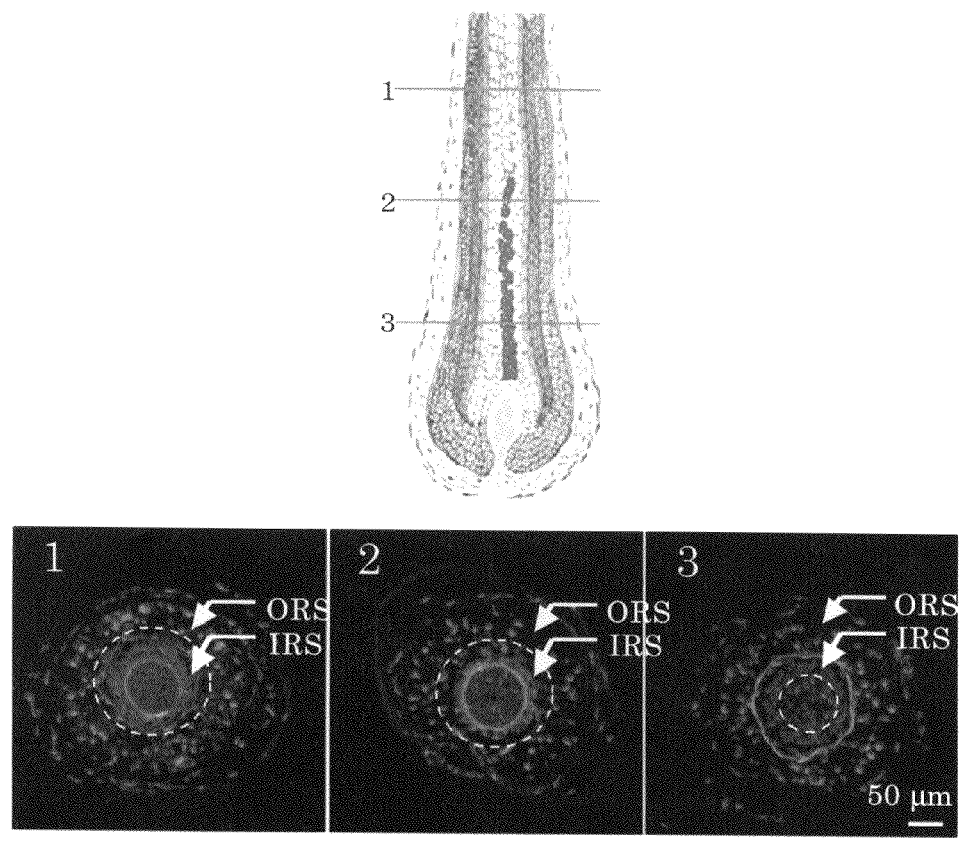
FIG. 7. Expression of β-galactosidase on organ culturing day 14.
Figure 8:
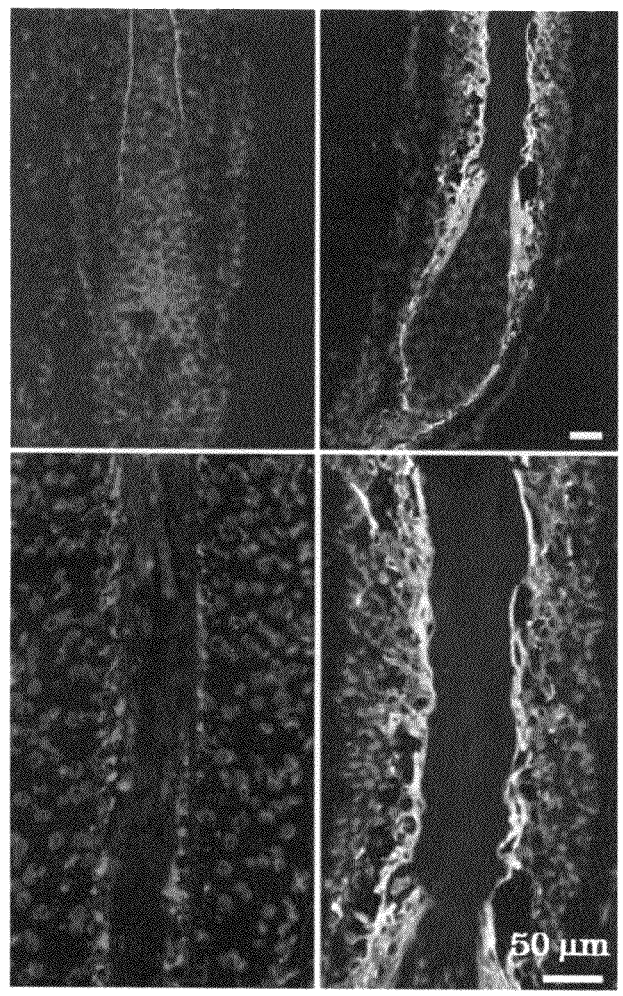
FIG. 8. Expression of β-galactosidase in the outer root sheath on organ culturing day 14:
  red: β-galactosidase;
  green: keratin 17 (marker of outer root sheath); and
  a unit bar: 50 μm.
Figure 9:
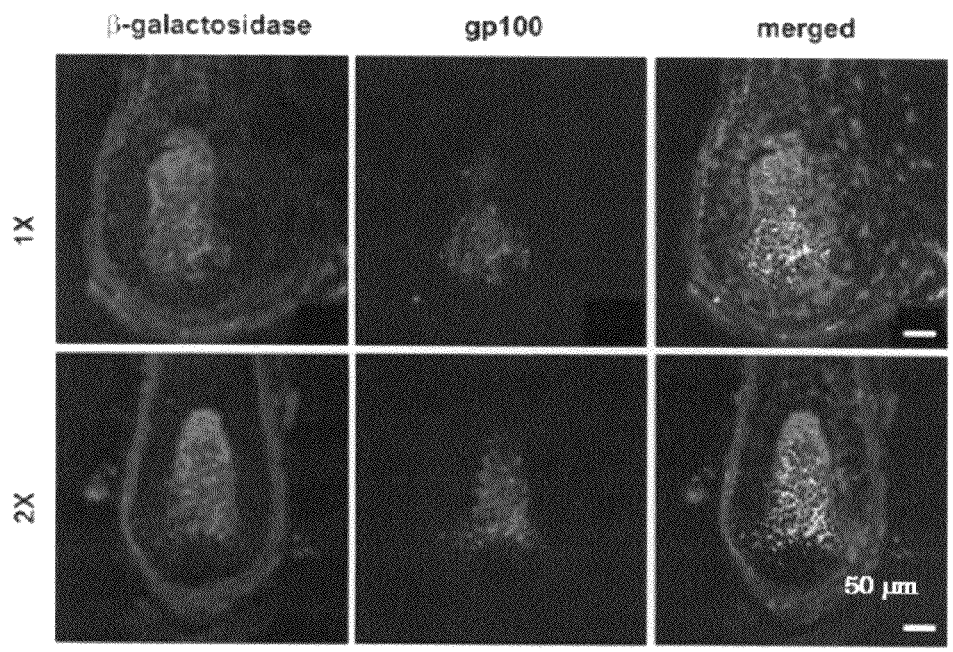
FIG. 9. Expression of β-galactosidase in a melanocyte present in a hair follicle on organ culturing day 7:
  red: β-galactosidase;
  green: gp100 (marker of melanocyte);
  upper: hair follicle transfected once; and
  lower: hair follicle transfected twice.

The results are shown in FIGS. 7 to 9. On day 14 of organ culturing, red-colored (positive) area was observed in the outer root sheath (ORS) and the inner root sheath (IRS), and the color density increased as the distance from the hair bulb to the observation site increased (FIG. 7). Separately, a section cut along the perpendicular direction was prepared, and gene expression was analyzed by use of an antibody specific for keratin 17 serving as a marker to the outer root sheath (ORS) and an antibody to β-galactosidase. Yellow-colored (positive) area, representing co-expression of both proteins, was observed in the entirety of the ORS of a hair follicle (FIG. 8). When an antibody HMB45 to melanosome (gp100) in a melanocyte and an antibody to β-galactosidase were used, yellow-colored (positive) area, representing co-expression of both proteins, was observed in a matrix region in which melanocytes are present on day 7 of organ culturing (FIG. 9).

Example 4

Copy Number of Exogenous Gene

Figure 10:
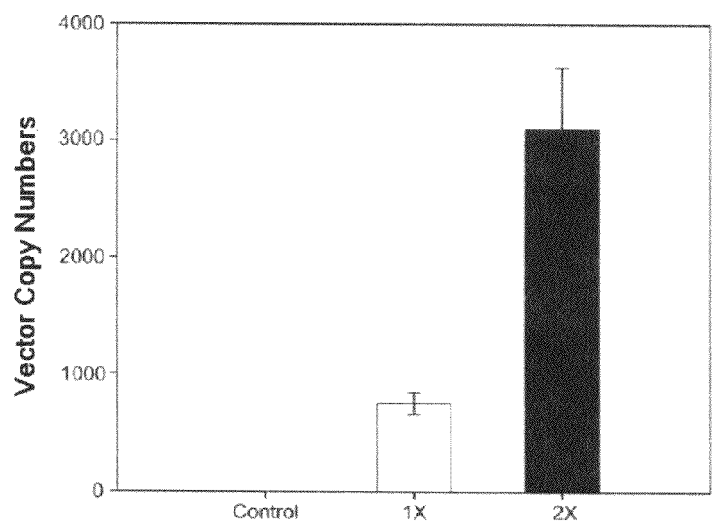
FIG. 10. Copy number of exogenous gene (from initial transfection to hour 48) in a non-transfected hair follicle (control), a hair follicle transfected once, and a hair follicle transfected twice.

Twenty-four hours after the second transfection, genomic DNA and vector DNA were extracted from the hair follicular organ by means of a DNeasy mini kit (Qiagen, Valencia, Calif.). The copy number of the exogenous gene was determined by means of TaqMan® probe (Applied Biosystems) which is specific to β-galactosidase transferred, and an ABI PRISM 7300 sequence detection system (Applied Biosystems). As a result, the copy number of the exogenous gene in the hair follicle transfected twice was found to be considerably higher as compared with the case of the hair follicle transfected once (FIG. 10).

Example 5

Analysis of a Transgene in Mice to which Transformed Hair Follicles have been Transplanted About three months after transplant, hair of human hair follicle origin was regenerated. At the time of hair regeneration, hair follicles were recovered, and a hair follicle was cut along a perpendicular direction, to thereby prepare sections. Gene expression sites of each section were investigated by use of an antibody to β-galactosidase.

Figure 11:
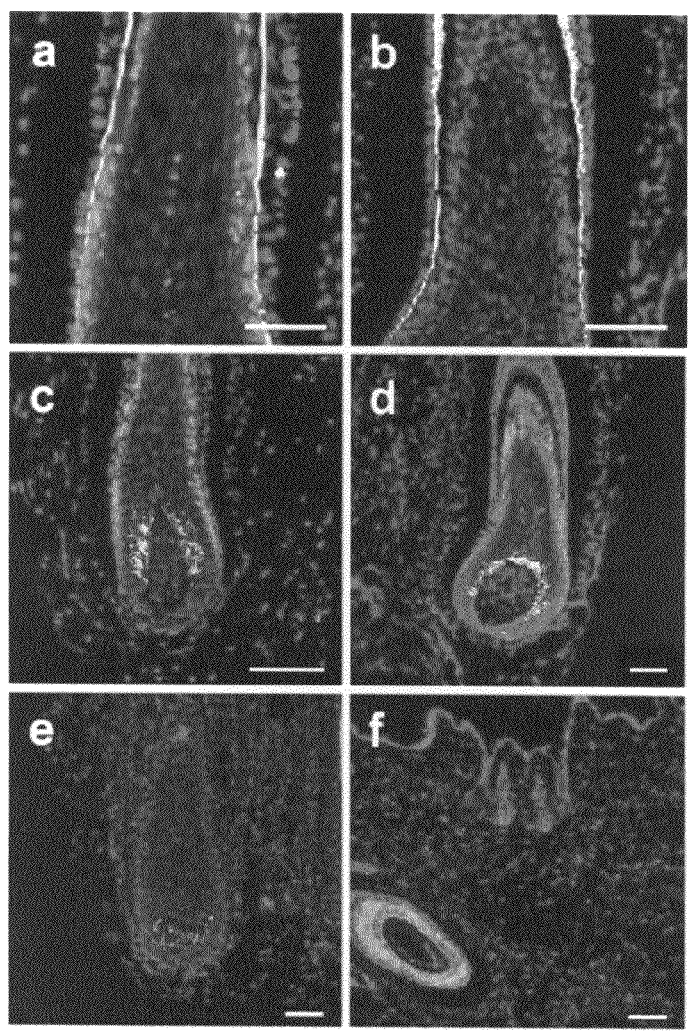
FIG. 11. Expression of β-galactosidase in a hair follicle regenerated about three months after transplanting twice-transfected transformed hair follicle:
  a: Caucasian straight hair follicles were transplanted;
  red: β-galactosidase;
  green: keratin 17 (marker of outer root sheath); and
  a unit bar: 50 μm;
  b: Caucasian curly hair follicles were transplanted;
  red: β-galactosidase;
  green: keratin 17 (marker of outer root sheath); and
  a unit bar: 50 μm;
  c: Caucasian straight hair follicles were transplanted;
  red: β-galactosidase;
  green: gp100 (marker of melanocyte); and
  a unit bar: 100 μm;
  d: Caucasian curly hair follicles were transplanted;
  red: β-galactosidase;
  green: gp100 (marker of melanocyte); and
  a unit bar: 100 μm;
  e: Non-transfected Caucasian straight hair follicles were transplanted;
  red: β-galactosidase;
  green: gp100 (marker of melanocyte); and
  a unit bar: 100 μm; and
  f: Caucasian curly hair follicles were transplanted;
  red: β-galactosidase; and
  a unit bar: 100 μm.

Specifically, straight hair follicles (FIG. 11a) and curly hair follicles (FIG. 11b), which had been regenerated about three months after transplant, were cut along a perpendicular direction, to thereby prepare sections, and gene expression was analyzed by use of an antibody specific for keratin 17 and an antibody to β-galactosidase. As a result, β-galactosidase was found to be expressed in the inner root sheath (IRS), outer root sheath (ORS), and medulla. Furthermore, when HMB45 and an antibody to β-galactosidase were used, yellow-colored (positive) area, representing co-expression of both proteins, was observed in a matrix region in which melanocytes are present (FIGS. 11c and 11d). Protein expression from the exogenous gene was also found in hair follicular keratinocytes and melanocytes three months after transplant, indicating that the exogenous gene was transferred to stem cells.

In contrast, β-galactosidase positive area was not observed in hair follicles regenerated from untreated hair follicles (FIG. 11e). However, unexpectedly, very small β-galactosidase positive area was observed in the hair bulb of some mouse hair follicles in the vicinity of a transfected human hair follicle (FIG. 11f; human hair follicle (lower left) and mouse hair follicle (center)), indicating that a part of human cells to which an exogenous gene had been transferred moved toward mouse hair follicles.

The invention claimed is:

1. A method of transforming a hair follicle stem cell, the method comprising:
   (a) collecting a tissue sample containing a hair follicle from the skin of a mammal;
   (b) trimming the tissue so that said sample consists essentially of a hair follicle;
   (c) contacting the tissue of step (b) with a VSV-G pseudotyped lentiviral vector in the absence of a collagenase treatment, wherein the lentiviral vector comprises an exogenous gene; and
   (d) culturing the tissue of step (c) in hair follicular organ culture medium such that a hair follicle stem cell in the bulge region of the hair follicle is transformed and expresses the exogenous gene.

2. The method of claim 1, wherein the mammal is human.

3. A method of transferring a gene into a mammal, the method comprising:
   (a) collecting a tissue sample containing a hair follicle from the skin of a mammal;
   (b) trimming the tissue so that said sample consists essentially of a hair follicle;
   (c) contacting the tissue of step (b) with a VSV-G pseudotyped lentiviral vector in the absence of collagenase treatment, wherein the lentiviral vector comprises an exogenous gene;
   (d) culturing the tissue of step (c) in hair follicular organ culture medium such that a hair follicle stem cell in the bulge region of the hair follicle is transformed and expresses the exogenous gene; and
   (e) transplanting the transformed hair follicle of step d) into a recipient mammal.

4. The method according to claim 3, wherein the hair follicle is of human origin.

5. A method for determining whether a transfected gene changes the shape or property of hair, the method comprising:
   (a) collecting a tissue sample containing a hair follicle from the skin of a mammal;
   (b) trimming the tissue so that said sample consists essentially of a hair follicle;
   (c) contacting the tissue of step (b) with a VSV-G pseudotyped lentiviral vector in the absence of collagenase treatment, wherein the lentiviral vector comprises an exogenous gene; and
   (d) culturing the tissue of step (c) in hair follicular organ culture medium such that a hair follicle stem cell in the bulge region of the hair follicle is transformed and expresses the exogenous gene;
   (e) transplanting the transformed hair follicle of step d) into a recipient mammal; and
   (f) determining whether the expression of said gene changes the shape or property of the hair.

6. The method of claim 1, wherein (c) and (d) are performed 2 or 3 times.

7. The method of claim 1 or 3, wherein expression of said gene is detectable three months after transplantation of said transformed hair follicle.

8. The method of claim 5, wherein expression of said gene is detectable three months after transplantation of said transformed hair follicle.

9. The method of claim 5, wherein the hair follicle is of human origin.

10. The method of claim 1, 3, or 5, which results in the expression of said gene in hair follicle keratinocytes and melanocytes.

11. The method of claim 3 or 5, which results in the expression of said gene in a hair bulb of said recipient mammal.

12. The method of claim 2, 4, or 9, wherein the hair follicle is of human scalp origin.

* * * * *